United States Patent
Debeaud et al.

(10) Patent No.: US 10,617,625 B2
(45) Date of Patent: *Apr. 14, 2020

(54) COMPOSITION COMPRISING POLYMER PARTICLES AND A MINERAL THICKENER, AND PROCESS USING THE SAME

(71) Applicant: L'OREAL, Paris (FR)

(72) Inventors: Roshanak Debeaud, L'hay les Roses (FR); Hong Li, Paris (FR); Stephane Douezan, Le Kremlin Bicetre (FR); Sylvie Manet, Verrieres le Buisson (FR); Veronique Ferrari, Maisons-Alfort (FR)

(73) Assignee: L'OREAL, Paris (FR)

( * ) Notice: Subject to any disclaimer, the term of this patent is extended or adjusted under 35 U.S.C. 154(b) by 227 days.

This patent is subject to a terminal disclaimer.

(21) Appl. No.: 15/534,216

(22) PCT Filed: Dec. 17, 2015

(86) PCT No.: PCT/EP2015/080184
§ 371 (c)(1),
(2) Date: Jun. 8, 2017

(87) PCT Pub. No.: WO2016/097119
PCT Pub. Date: Jun. 23, 2016

(65) Prior Publication Data
US 2017/0360682 A1    Dec. 21, 2017

(30) Foreign Application Priority Data

Dec. 18, 2014 (FR) .................... 14 62721

(51) Int. Cl.
| | | |
|---|---|---|
| *A61K 8/81* | (2006.01) | |
| *A61K 8/02* | (2006.01) | |
| *A61K 8/25* | (2006.01) | |
| *A61K 8/31* | (2006.01) | |
| *A61Q 1/00* | (2006.01) | |
| *A61Q 1/02* | (2006.01) | |
| *A61Q 1/06* | (2006.01) | |
| *A61Q 1/10* | (2006.01) | |

(52) U.S. Cl.
CPC .......... *A61K 8/8147* (2013.01); *A61K 8/0241* (2013.01); *A61K 8/25* (2013.01); *A61K 8/31* (2013.01); *A61K 8/8152* (2013.01); *A61Q 1/00* (2013.01); *A61Q 1/02* (2013.01); *A61Q 1/06* (2013.01); *A61Q 1/10* (2013.01); *A61K 2800/10* (2013.01); *A61K 2800/31* (2013.01); *A61K 2800/52* (2013.01)

(58) Field of Classification Search
None
See application file for complete search history.

(56) References Cited

U.S. PATENT DOCUMENTS

| | | | |
|---|---|---|---|
| 5,616,598 A | 4/1997 | Lion et al. | |
| 5,851,517 A | 12/1998 | Mougin et al. | |
| 5,945,095 A | 8/1999 | Mougin et al. | |
| 9,918,925 B2 * | 3/2018 | Debaud .................. | A61K 8/31 |
| 9,943,475 B2 * | 4/2018 | Debeaud .................. | A61K 8/31 |
| 2004/0137028 A1 | 7/2004 | de la Poterie | |
| 2011/0243864 A1 | 10/2011 | Farcet et al. | |

FOREIGN PATENT DOCUMENTS

| | | |
|---|---|---|
| EP | 0 749 746 | 12/1996 |
| EP | 0 749 747 | 12/1996 |
| EP | 1 586 300 A1 | 10/2005 |
| FR | 2 785 530 | 5/2000 |
| FR | 2 937 645 | 4/2010 |
| FR | 2 949 675 A1 | 3/2011 |
| FR | 2 972 630 A1 | 9/2012 |
| FR | 2 972 631 A1 | 9/2012 |

OTHER PUBLICATIONS

International Search Report dated Feb. 19, 2016 in PCT/EP2015/080184 filed Dec. 17, 2015.
U.S. Appl. No. 14/575,259, filed Dec. 18, 2014, U.S. Pat. No. 2016/0175204, Rita Jaky El-Khouri.
U.S. Appl. No. 14/575,419, filed Dec. 18, 2014, U.S. Pat. No. 2016/0175230, Susan Halpern-Chirch.
U.S. Appl. No. 14/575,866, filed Dec. 18, 2014, U.S. Pat. No. 2016/0175232, Rita Jaky El-Khouri.
U.S. Appl. No. 14/974,531, filed Dec. 18, 2015, U.S. Pat. No. 2016/0184211, Roshanak Debeaud.
U.S. Appl. No. 14/974,706, filed Dec. 18, 2015, U.S. Pat. No. 2016/0175205, Roshanak Debeaud.
U.S. Appl. No. 15/105,293, filed Jun. 16, 2016, U.S. Pat. No. 2016/0317423, Julien Portal.

(Continued)

*Primary Examiner* — Bethany P Barham
*Assistant Examiner* — Barbara S Frazier
(74) *Attorney, Agent, or Firm* — Oblon, McClelland, Maier & Neustadt, L.L.P.

(57) ABSTRACT

The present invention relates to a composition comprising particles of a polymer that is surface-stabilized with a stabilizer, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4, at least one hydrocarbon-based oil and at least one mineral thickener chosen from optionally modified clays and optionally modified silicas, or mixtures thereof. The invention also relates to a process for making up and/or caring for keratin materials, in which said composition is applied.

20 Claims, No Drawings

(56) References Cited

OTHER PUBLICATIONS

U.S. Appl. No. 15/533,444, filed Jun. 6, 2017, Hong Li.
U.S. Appl. No. 15/537,082, filed Jun. 16, 2017, Laure Daubersies.
U.S. Appl. No. 15/537,422, Philippe Ilekti.
U.S. Appl. No. 15/537,423, Philippe Ilekti.
U.S. Appl. No. 15/535,963, filed Jun. 14, 2017, Laure Daubersies.

* cited by examiner

COMPOSITION COMPRISING POLYMER PARTICLES AND A MINERAL THICKENER, AND PROCESS USING THE SAME

CROSS REFERENCE TO RELATED APPLICATIONS

This application is the national stage of PCT/EP2015/080184, filed Dec. 17, 2015, the disclosure of which is incorporated herein by reference in its entirety. The parent application claims priority to French Application No. 1462721, filed Dec. 18, 2014, the disclosure of which is incorporated herein by reference in its entirety.

BACKGROUND OF THE INVENTION

Field of the Invention

The present invention relates to compositions for making up and/or caring for human keratin materials, such as the skin, the lips and keratin fibres especially such as the eyelashes, comprising polymer particles and at least one particular mineral thickener.

These compositions are well known and, although they have specific properties as a function of their use, there has been a very clear tendency in recent years to develop compositions whose persistence is improved. This avoids, on the one hand, the need to reapply the composition too often and, on the other hand, reduces transfer onto supports with which the made-up areas might come into contact (clothing, cups, etc.) or else their removal via the action of external agents (sebum, food, rain, etc.).

That is why the compositions for which this property is sought generally comprise at least one film-forming agent. This agent is quite often a polymer, which is in a solubilized form or dispersed in one of the phases of the composition. It allows the composition, once applied, to form after drying a film that is more cohesive and persistent on the support.

One of the problems encountered with such film-forming agents lies in the fact that the resulting compositions give a deposit that may be considered as too tacky, quite often giving rise to difficulties in correctly applying the composition.

Compositions are thus sought comprising at least one film-forming agent, which make it possible to obtain, after application, a film with good cosmetic properties, especially such as good persistence, and which is non-tacky.

SUMMARY OF THE INVENTION

One subject of the invention is thus a composition comprising particles of at least one polymer that is surface-stabilized with a stabilizer, the polymer of the particles being a $C_1$-$C_4$ alkyl (meth)acrylate polymer; the stabilizer being an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4, at least one hydrocarbon-based oil and at least one mineral thickener chosen from optionally modified clays and optionally modified silicas, or mixtures thereof.

A subject of the invention is also a process for making up and/or caring for keratin materials, in particular the skin, the lips and keratin fibres especially such as the eyelashes and the eyebrows, which consists in applying said composition.

DETAILED DESCRIPTION OF THE PREFERRED EMBODIMENTS

It has in fact been observed that the composition has the advantage of applying as a homogeneous, non-tacky deposit, which has very good persistence, and in particular very good transfer resistance properties, including transfer resistance in the presence of sebum.

Moreover, and this represents a particularly interesting advantage in the context of compositions for making up the eyelashes, such as mascaras, it has been found that it is possible to remove the composition without leaving unsightly coloured marks. Thus, their removal can take place by sheath, in other words in cohesive pieces that do not stain the neighbouring skin. In addition, these compositions can give the eyelashes volume, since it is possible to have a sufficiently thick deposit that is water-resistant.

However, other advantages will emerge more clearly on reading the description and the examples that follow.

It should be noted that, in the remainder of the description, unless otherwise indicated, the limits indicated for a range are included in that range.

The expressions "at least one" and "several" are used without distinction.

Hydrocarbon-Based Oil

The composition according to the invention comprises a hydrocarbon-based oil.

This oil may be volatile (vapour pressure greater than or equal to 0.13 Pa measured at 25° C.) or non-volatile (vapour pressure less than 0.13 Pa measured at 25° C.).

Preferably, the hydrocarbon-based oil is volatile.

The hydrocarbon-based oil is an oil (non-aqueous compound) that is liquid at room temperature (25° C.).

The term "hydrocarbon-based oil" means an oil formed essentially from, or even consisting of, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be chosen from:
hydrocarbon-based oils containing from 8 to 16 carbon atoms, and especially:
branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade name Isopar or Permethyl,
linear alkanes, for instance n-dodecane ($C_{12}$) and n-tetradecane ($C_{14}$) sold by Sasol under the respective references Parafol 12-97 and Parafol 14-97, and also mixtures thereof, the undecane-tridecane mixture, the mixtures of n-undecane ($C_{11}$) and of n-tridecane ($C_{13}$) obtained in Examples 1 and 2 of patent application WO 2008/155 059 from the company Cognis, and mixtures thereof,
short-chain esters (containing from 3 to 8 carbon atoms in total) such as ethyl acetate, methyl acetate, propyl acetate or n-butyl acetate,
hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passionflower oil and musk rose oil; shea butter; or else caprylic/capric acid triglycerides, for instance those sold by the company Stéarineries Dubois or those sold under the names Miglyol 810®, 812® and 818® by the company Dynamit Nobel, synthetic ethers containing from 10 to 40 carbon atoms;

linear or branched hydrocarbons of mineral or synthetic origin, such as petroleum jelly, polydecenes, hydrogenated polyisobutene such as Parleam®, squalane and liquid paraffins, and mixtures thereof, synthetic esters such as oils of formula $R_1COOR_2$ in which $R_1$ represents a linear or branched fatty acid residue containing from 1 to 40 carbon atoms and $R_2$ represents an, in particular, branched hydrocarbon-based chain containing from 1 to 40 carbon atoms, on the condition that $R_1+R_2$ 10, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol, a mixture thereof.

More particularly, the content of hydrocarbon-based oil(s) ranges from 20% to 75% by weight, more particularly from 30% to 75% by weight and preferably from 40% to 60% by weight, relative to the weight of the composition.

This hydrocarbon-based oil may be provided totally or partly with the surface-stabilized polymer particles, in particular when these particles are introduced into the composition in the form of a pre-prepared dispersion of surface-stabilized polymer particles. In this case, the hydrocarbon-based oil present in the composition represents at least the non-aqueous medium of the dispersion of surface-stabilized polymer particles.

Advantageously, the hydrocarbon-based oil is apolar (thus formed solely from carbon and hydrogen atoms).

The hydrocarbon-based oil is preferably chosen from hydrocarbon-based oils containing from 8 to 16 carbon atoms and better still from 12 to 16 carbon atoms, in particular the apolar oils described previously.

Preferentially, the hydrocarbon-based oil is isododecane. More particularly, the isododecane content ranges from 20% to 75% by weight, more particularly from 30% to 75% by weight and preferably from 40% to 60% by weight, relative to the weight of the composition.

Preferably, the hydrocarbon-based oil(s), in particular isododecane, constitute the only oil(s) of the composition, or are present in a predominant weight content relative to the other oil(s) that may be present in the composition.

In accordance with a particular embodiment of the invention, if the composition contains one or more non-volatile oils, their content advantageously does not exceed 20% by weight, more particularly does not exceed 10% by weight, preferably does not exceed 5% by weight relative to the weight of the composition, and better still does not exceed 2% by weight relative to the weight of the composition, or even is free of non-volatile oil(s).

Polymer Particles

The composition according to the invention moreover comprises particles, which are generally spherical, of at least one surface-stabilized polymer.

Preferably, the particles are introduced into the composition in the form of a dispersion of particles, which are generally spherical, of at least one surface-stabilized polymer, in an oily (or non-aqueous) medium, advantageously containing at least one hydrocarbon-based oil, as defined previously.

The polymer of the particles is a $C_1$-$C_4$ alkyl (meth)acrylate polymer.

The $C_1$-$C_4$ alkyl (meth)acrylate monomers may be chosen from methyl (meth)acrylate, ethyl (meth)acrylate, n-propyl (meth)acrylate, isopropyl (meth)acrylate, n-butyl (meth)acrylate and tert-butyl (meth)acrylate.

A $C_1$-$C_4$ alkyl acrylate monomer is advantageously used. Preferentially, the polymer of the particles is a methyl acrylate and/or ethyl acrylate polymer.

The polymer of the particles may also comprise an ethylenically unsaturated acid monomer or the anhydride thereof, chosen especially from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof.

Preferably, the ethylenically unsaturated acid monomer is chosen from (meth)acrylic acid, maleic acid and maleic anhydride.

The salts may be chosen from salts of alkali metals, for example sodium or potassium; salts of alkaline-earth metals, for example calcium, magnesium or strontium; metal salts, for example zinc, aluminium, manganese or copper; ammonium salts of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

The polymer of the particles may thus comprise or consist essentially of 80% to 100% by weight of $C_1$-$C_4$ alkyl (meth)acrylate and of 0 to 20% by weight of ethylenically unsaturated acid monomer, relative to the total weight of the polymer.

According to a first embodiment of the invention, the polymer consists essentially of a polymer of one or more $C_1$-$C_4$ alkyl (meth)acrylate monomers.

According to a second embodiment of the invention, the polymer consists essentially of a copolymer of $C_1$-$C_4$ (meth) acrylate and of (meth)acrylic acid or maleic anhydride.

The polymer of the particles may be chosen from:
methyl acrylate homopolymers
ethyl acrylate homopolymers
methyl acrylate/ethyl acrylate copolymers
methyl acrylate/ethyl acrylate/acrylic acid copolymers
methyl acrylate/ethyl acrylate/maleic anhydride copolymers
methyl acrylate/acrylic acid copolymers ethyl acrylate/acrylic acid copolymers
methyl acrylate/maleic anhydride copolymers
ethyl acrylate/maleic anhydride copolymers.

Advantageously, the polymer of the particles is a non-crosslinked polymer.

The polymer of the particles preferably has a number-average molecular weight ranging from 2000 to 10 000 000 and preferably ranging from 150 000 to 500 000.

In the case of a particle dispersion, the polymer of the particles may be present in the dispersion in a content ranging from 21% to 58.5% by weight and preferably ranging from 36% to 42% by weight, relative to the total weight of the dispersion.

The stabilizer is an isobornyl (meth)acrylate polymer chosen from isobornyl (meth)acrylate homopolymer and statistical copolymers of isobornyl (meth)acrylate and of $C_1$-$C_4$ alkyl (meth)acrylate present in an isobornyl (meth)acrylate/$C_1$-$C_4$ alkyl (meth)acrylate weight ratio of greater than 4, preferably greater than 4.5 and even more advantageously greater than or equal to 5. Advantageously, said weight ratio ranges from 4.5 to 19, preferably from 5 to 19 and more particularly from 5 to 12.

Advantageously, the stabilizer is chosen from:
isobornyl acrylate homopolymers
statistical copolymers of isobornyl acrylate/methyl acrylate
statistical copolymers of isobornyl acrylate/methyl acrylate/ethyl acrylate
statistical copolymers of isobornyl methacrylate/methyl acrylate
in the weight ratio described previously.

Preferably, the stabilizer is soluble in the hydrocarbon-based oil(s), in particular soluble in isododecane.

The stabilizing polymer preferably has a number-average molecular weight ranging from 10 000 to 400 000 and preferably ranging from 20 000 to 200 000.

The stabilizer is in contact with the surface of the polymer particles and thus makes it possible to stabilize these particles at the surface, in particular in order to keep these particles in dispersion in the non-aqueous medium of the dispersion.

According to a theory which should not limit the scope of the present invention, the inventors put forward the hypothesis that the surface stabilization of the $C_1$-$C_4$ alkyl (meth)acrylate polymer particles results from a phenomenon of surface adsorption of the stabilizer onto the $C_1$-$C_4$ alkyl (meth)acrylate polymer particles.

Advantageously, the combination of the stabilizer+polymer of the particles present in particular in particular in the dispersion comprises from 10% to 50% by weight of polymerized isobornyl (meth)acrylate and from 50% to 90% by weight of polymerized $C_1$-$C_4$ alkyl (meth)acrylate, relative to the total weight of the combination of the stabilizer+polymer of the particles.

Preferentially, the combination of the stabilizer+polymer of the particles present in particular in the dispersion comprises from 15% to 30% by weight of polymerized isobornyl (meth)acrylate and from 70% to 85% by weight of polymerized $C_1$-$C_4$ alkyl (meth)acrylate, relative to the total weight of the combination of the stabilizer+polymer of the particles.

When the polymer particles are provided in the composition in the form of a pre-prepared dispersion, the oily medium of this polymer dispersion comprises a hydrocarbon-based oil. Reference may be made to that which has been indicated previously concerning this oil as regards its nature.

Advantageously, the hydrocarbon-based oil is apolar and preferably chosen from hydrocarbon-based oils containing from 8 to 16 carbon atoms, in particular the apolar oils described previously.

Preferentially, the hydrocarbon-based oil is isododecane.

The polymer particles, in particular in the dispersion, preferably have an average size, especially a number-average size, ranging from 50 to 500 nm, especially ranging from 75 to 400 nm and better still ranging from 100 to 250 nm.

In general, a dispersion of surface-stabilized polymer particles that is suitable for use in the invention may be prepared in the following manner, which is given as an example.

The polymerization may be performed in dispersion, i.e. by precipitation of the polymer during formation, with protection of the formed particles with a stabilizer.

In a first step, the stabilizing polymer is prepared by mixing the constituent monomer(s) of the stabilizing polymer, with a free-radical initiator, in a solvent known as the synthesis solvent, and by polymerizing these monomers. In a second step, the constituent monomer(s) of the polymer of the particles are added to the stabilizing polymer formed and polymerization of these added monomers is performed in the presence of the free-radical initiator.

When the non-aqueous medium is a non-volatile hydrocarbon-based oil, the polymerization may be performed in an apolar organic solvent (synthesis solvent), followed by adding the non-volatile hydrocarbon-based oil (which should be miscible with said synthesis solvent) and selectively distilling off the synthesis solvent.

A synthesis solvent which is such that the monomers of the stabilizing polymer and the free-radical initiator are soluble therein, and the polymer particles obtained are insoluble therein, so that they precipitate therein during their formation, is thus chosen.

In particular, the synthesis solvent may be chosen from alkanes such as heptane or cyclohexane.

When the non-aqueous medium is a volatile hydrocarbon-based oil, the polymerization may be performed directly in said oil, which thus also acts as synthesis solvent. The monomers should also be soluble therein, as should the free-radical initiator, and the polymer of the particles obtained should be insoluble therein.

The monomers are preferably present in the synthesis solvent, before polymerization, in a proportion of 5-20% by weight. The total amount of monomers may be present in the solvent before the start of the reaction, or part of the monomers may be added gradually as the polymerization reaction proceeds.

The free-radical initiator may especially be azobisisobutyronitrile or tert-butyl peroxy-2-ethylhexanoate.

The polymerization may be performed at a temperature ranging from 70 to 110° C.

The polymer particles are surface-stabilized, when they are formed during the polymerization, by means of the stabilizer.

The stabilization may be performed by any known means, and in particular by direct addition of the stabilizer, during the polymerization.

The stabilizer is preferably also present in the mixture before polymerization of the monomers of the polymer of the particles. However, it is also possible to add it continuously, especially when the monomers of the polymer of the particles are also added continuously.

From 10% to 30% by weight and preferably from 15% to 25% by weight of stabilizer may be used relative to the total weight of monomers used (stabilizer+polymer of the particles).

The polymer particle dispersion advantageously comprises from 30% to 65% by weight and preferably from 40% to 60% by weight of solids, relative to the total weight of the dispersion.

Moreover, the composition according to the invention advantageously comprises a content of surface-stabilized polymer particles, expressed as active material, of between 5% and 55% by weight, more particularly between 5% and 50% by weight, preferably between 8% and 45% by weight and even more preferentially between 10% and 40% by weight relative to the weight of the composition.

Mineral Thickener

The composition according to the invention comprises at least one mineral thickener chosen from optionally modified clays and optionally modified silicas, or mixtures thereof.

More particularly, the content of mineral thickener, expressed as active material, represents from 0.5% to 30% by weight, preferably from 0.5% to 20% by weight and even more preferentially between 1% and 15% by weight, relative to the weight of the composition.

In accordance with an advantageous embodiment of the invention, the content of mineral thickener is such that the weight ratio, expressed as active material, of polymer particles/thickener ranges from 0.5 to 80, preferentially from 5 to 50 and even more particularly from 10 to 30.

i) Optionally Modified Clays

Clays are silicates containing a cation that may be chosen from calcium, magnesium, aluminium, sodium, potassium and lithium cations, and mixtures thereof.

Examples of such products that may be mentioned include clays of the smectite family, and also of the vermiculite, stevensite and chlorite families. These clays can be of natural or synthetic origin.

Mention may more particularly be made of smectites, such as saponites, hectorites, montmorillonites, bentonites or beidellite and in particular synthetic hectorites (also known as laponites), such as the products sold by Rockwood Additives Limited under the names Laponite® XLS, Laponite® XLG, Laponite® RD, Laponite® RDS and Laponite® XL21 (these products are sodium magnesium silicates and in particular sodium lithium magnesium silicates); bentonites, such as the product sold under the name Bentone HC by Rheox; magnesium aluminium silicates, which are in particular hydrated, such as the products sold by Vanderbilt Company under the name Veegum Ultra, Veegum HS or Veegum DGT, or also calcium silicates and in particular that in synthetic form sold by the company under the name Micro-Cel C.

Preferably, use is made of organophilic clays, more particularly modified clays, such as montmorillonite, bentonite, hectorite, attapulgite and sepiolite, and mixtures thereof. The clay is preferably a bentonite or a hectorite.

These clays are modified with a chemical compound chosen from quaternary amines, tertiary amines, amine acetates, imidazolines, amine soaps, fatty sulfates, alkylarylsulfonates and amine oxides, and mixtures thereof.

Mention may thus be made of hectorites modified with a quaternary amine, more specifically with a $C_{10}$ to $C_{22}$ fatty acid ammonium halide, such as a chloride, such as hectorite modified with distearyldimethylammonium chloride (CTFA name: Disteardimonium hectorite), for instance the product sold under the name Bentone 38V®, Bentone 38V CG or Bentone EW CE by the company Elementis, or stearalkonium hectorites, such as Bentone 27 V.

Mention may also be made of quaternium-18 bentonites, such as those sold under the names Bentone 34 by the company Elementis, Tixogel VP by the company United Catalyst and Claytone 40 by the company Southern Clay; stearalkonium bentonites, such as those sold under the names Tixogel LG by the company United Catalyst and Claytone AF and Claytone APA by the company Southern Clay; or quaternium-18/benzalkonium bentonites, such as that sold under the name Claytone HT by the company Southern Clay.

According to a preferred embodiment, the thickener is chosen from organophilic modified clays, in particular organophilic modified hectorites, in particular modified with benzyldimethylammonium stearate chloride or with distearyldimethylammonium chloride.

In accordance with one variant of the invention, the content of optionally modified clay ranges from 0.5% to 10% by weight relative to the weight of the composition, expressed as active material.

ii) Optionally Modified Silicas

Mention may also be made of fumed silica optionally subjected to a hydrophobic surface treatment, the particle size of which is less than 1 μm. Specifically, it is possible to chemically modify the surface of the silica, by chemical reaction generating a reduced number of silanol groups present at the surface of the silica. Silanol groups can in particular be replaced by hydrophobic groups: a hydrophobic silica is then obtained. The hydrophobic groups may be:

trimethylsiloxyl groups, which are obtained especially by treating fumed silica in the presence of hexamethyldisilazane. Silicas thus treated are known as "silica silylate" according to the CTFA ($6^{th}$ edition, 1995). They are sold, for example, under the references Aerosil R812® by the company Degussa, and Cab-O-Sil TS-530® by the company Cabot;

dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold, for example, under the references Aerosil R972® and Aerosil R974® by the company Degussa, and Cab-O-Sil TS-610® and Cab-O-Sil TS-720® by the company Cabot.

The hydrophobic fumed silica in particular has a particle size that may be nanometric to micrometric, for example ranging from about 5 to 200 nm.

The composition according to the invention may comprise or comprises at least silica aerogel particles.

Silica aerogels are porous materials obtained by replacing (by drying) the liquid component of a silica gel with air.

They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles used in the present invention have a specific surface area per unit mass ($S_M$) ranging from 500 to 1500 m²/g, preferably from 600 to 1200 m²/g and better still from 600 to 800 m²/g, and a size expressed as the volume mean diameter (D[0.5]) ranging from 1 to 1500 μm, better still from 1 to 1000 μm, preferably from 1 to 100 µm, in particular from 1 to 30 µm, more preferably from 5 to 25 µm, better still from 5 to 20 µm and even better still from 5 to 15 µm.

According to one embodiment, the hydrophobic silica aerogel particles used in the present invention have a size expressed as volume-mean diameter (D[0.5]) ranging from 1 to 30 µm, preferably from 5 to 25 µm, better still from 5 to 20 µm and even better still from 5 to 15 µm.

The specific surface area per unit mass may be determined by the nitrogen absorption method, known as the BET (Brunauer-Emmett-Teller) method, described in The Journal of the American Chemical Society, vol. 60, page 309, February 1938, which corresponds to international standard ISO 5794/1 (appendix D). The BET specific surface area corresponds to the total specific surface area of the particles under consideration.

The sizes of the silica aerogel particles may be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., *Light Scattering by Small Particles*, Chapters 9 and 10, Wiley, New York, 1957.

According to an advantageous embodiment, the hydrophobic silica aerogel particles used in the present invention have a specific surface area per unit mass ($S_M$) ranging from 600 to 800 m$^2$/g and a size expressed as the volume mean diameter (D[0.5]) ranging from 5 to 20 µm and even better still from 5 to 15 µm.

The silica aerogel particles used in the present invention can advantageously exhibit a packed density σ ranging from 0.02 g/cm$^3$ to 0.10 g/cm$^3$, preferably from 0.03 g/cm$^3$ to 0.08 g/cm$^3$ and preferably from 0.05 g/cm$^3$ to 0.08 g/cm$^3$.

In the context of the present invention, this density, known as the tapped density, may be assessed according to the following protocol:

40 g of powder are poured into a measuring cylinder; the measuring cylinder is then placed on a Stav 2003 machine from Stampf Volumeter; the measuring cylinder is then subjected to a series of 2500 tapping actions (this operation is repeated until the difference in volume between two consecutive tests is less than 2%); the final volume Vf of tapped powder is then measured directly on the measuring cylinder. The tapped density is determined by the ratio m/Vf, in this instance 40/Vf (Vf being expressed in cm$^3$ and m in g).

According to a preferred embodiment, the hydrophobic silica aerogel particles used in the present invention have a specific surface area per unit of volume $S_V$ ranging from 5 to 60 m$^2$/cm$^3$, preferably from 10 to 50 m$^2$/cm$^3$ and better still from 15 to 40 m$^2$/cm$^3$.

The specific surface area per unit of volume is given by the relationship: $S_V = S_M \times \sigma$, where σ is the tapped density, expressed in g/cm$^3$, and $S_M$ is the specific surface area per unit of mass, expressed in m$^2$/g, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The absorbing capacity measured at the wet point, noted Wp, corresponds to the amount of oil that needs to be added to 100 g of particles in order to obtain a homogeneous paste.

It is measured according to what is known as the wet point method or the method for determining the oil uptake of a powder described in standard NF T 30-022. It corresponds to the amount of oil adsorbed onto the available surface of the powder and/or absorbed by the powder by measurement of the wet point, described below:

An amount m=2 g of powder is placed on a glass plate, and the oil (isononyl isononanoate) is then added dropwise. After addition of 4 to 5 drops of oil to the powder, mixing is carried out using a spatula, and addition of oil is continued until conglomerates of oil and powder have formed. From this point, the oil is added at the rate of one drop at a time and the mixture is subsequently triturated with the spatula. The addition of oil is stopped when a firm, smooth paste is obtained. This paste must be able to be spread on the glass plate without cracking or forming lumps. The volume Vs (expressed in ml) of oil used is then noted.

The oil uptake corresponds to the ratio Vs/m.

The aerogels used according to the present invention are hydrophobic silica aerogels, preferably of silyl silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles that have been surface-modified by silylation, reference may be made to document U.S. Pat. No. 7,470,725.

Use will preferably be made of hydrophobic silica aerogel particles surface-modified with trimethylsilyl groups.

As hydrophobic silica aerogels that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 m$^2$/g.

Mention may also be made of the aerogels sold by the company Cabot under the references Aerogel TLD 201, Aerogel OGD 201, Aerogel TLD 203, Enova® Aerogel MT 1100 and Enova Aerogel MT 1200.

Use will preferably be made of the aerogel sold under the name VM-2270 (INCI name: Silica silylate) by the company Dow Corning, the particles of which have an average size ranging from 5-15 microns and a specific surface area per unit of mass ranging from 600 to 800 m$^2$/g.

Preferably, when the composition comprises at least one thickener chosen from optionally modified silicas, these silicas are chosen from hydrophobic silica aerogel particles.

In accordance with one variant of the invention, the content of optionally modified silica, expressed as active material, ranges from 0.5% to 20% by weight and more particularly from 0.5% to 15% by weight relative to the weight of the composition.

Preferably, the mineral thickeners are chosen from lipophilic (organophilic) clays, in particular modified hectorites; hydrophobic-treated fumed silica; hydrophobic silica aerogels, or mixtures thereof.

Preferably, the composition comprises at least one organophilic modified clay or at least one hydrophobic modified silica, in particular hydrophobic silica aerogels.

Additional Silicone Oils

The composition according to the invention may also comprise at least one additional volatile or non-volatile, and preferably volatile, silicone oil.

The term "silicone oil" means an oil containing at least one silicon atom, and especially containing Si—O groups.

Among the additional volatile silicone oils that are suitable for use, examples that may be mentioned include volatile linear or cyclic silicone oils, especially those with a viscosity 8 centistokes ($8 \times 10^{-6}$ m$^2$/s) and especially containing from 2 to 7 silicon atoms, these silicones optionally comprising alkyl or alkoxy groups containing from 1 to 10 carbon atoms.

As volatile silicone oils that may be used in the invention, mention may be made especially of octamethylcyclotetrasiloxane, cyclopentadimethylsiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As non-volatile silicone oils, mention may be made of non-phenyl non-volatile silicone oils, for instance polydimethylsiloxanes (PDMS), PDMSs comprising aliphatic groups, in particular alkyl or alkoxy, which are pendent and/or at the end of the silicone chain; these groups each comprising from 2 to 24 carbon atoms. An example that may be mentioned is cetyl dimethicone sold under the commercial reference Abil Wax 9801 from Evonik Goldschmidt.

Non-volatile phenyl silicone oils optionally comprising one or more dimethicone fragments (—(CH3)2-SiO—) are also suitable, for instance phenyl trimethicones, phenyl dimethicones, phenyltrimethylsiloxydiphenylsiloxanes, diphenyl dimethicones and trimethylpentaphenyltrisiloxane, and mixtures thereof.

If the composition comprises any, the content of additional, preferably volatile, silicone oil(s) is between 1% and 15% by weight relative to the weight of the composition.

Preferably, the composition does not comprise more than 10% by weight of additional non-volatile oil, relative to the weight of the composition, and preferably does not contain any.

Waxes

The composition according to the invention may optionally comprise at least one wax.

For the purposes of the present invention, the term "wax" means a lipophilic compound, which is solid at room temperature (25° C.), with a reversible solid/liquid change of state, which has a melting point of greater than or equal to 30° C. that may be up to 120° C.

The melting point of the wax may be measured using a differential scanning calorimeter (DSC), for example the calorimeter sold under the name DSC 30 by the company Mettler.

The waxes may be hydrocarbon-based waxes and/or silicone waxes, and may be of plant, mineral, animal and/or synthetic origin. In particular, the waxes have a melting point of greater than 25° C. and better still greater than 45° C.

Hydrocarbon-based waxes, for instance beeswax, lanolin wax or Chinese insect wax; rice wax, carnauba wax, candelilla wax, ouricury wax, esparto grass wax, cork fibre wax, sugar cane wax, Japan wax and sumach wax; montan wax, microcrystalline waxes, paraffins and ozokerite; polyethylene waxes, the waxes obtained by Fisher-Tropsch synthesis and waxy copolymers, and also esters thereof, may especially be used.

Mention may also be made of waxes obtained by catalytic hydrogenation of animal or plant oils containing linear or branched $C_8$-$C_{32}$ fatty chains.

Among these waxes that may in particular be mentioned are hydrogenated jojoba oil, isomerized jojoba oil such as the trans-isomerized partially hydrogenated jojoba oil manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate sold under the name Hest 2T-4S by the company Heterene, bis(1,1,1-trimethylolpropane) tetrabehenate sold under the name Hest 2T-4B by the company Heterene.

Mention may also be made of silicone waxes, for instance alkyl or alkoxy dimethicones containing from 16 to 45 carbon atoms, polypropylsilsesquioxane waxes (as described in patent WO 2005/100444), in particular with the C30-C45 alkyldimethylsilyl polypropylsilsesquioxane compound commercially available from Dow Corning under the brand name SW-8005 C30 Resin Wax.

The wax obtained by hydrogenation of olive oil esterified with the stearyl alcohol, sold under the name Phytowax Olive 18 L 57 or else the waxes obtained by hydrogenation of castor oil esterified with cetyl alcohol, sold under the names Phytowax Castor 16L64 and 22L73 by the company Sophim, may also be used. Such waxes are described in patent application FR-A-2 792 190.

If the composition comprises any, the content of wax may represent from 0.1% to 30% by weight and advantageously from 0.3% to 20% by weight relative to the weight of the composition.

In accordance with a particular embodiment of the invention, the content of wax does not exceed 10% by weight relative to the weight of the composition, and even more particularly does not exceed 5% by weight, relative to the weight of the composition. According to certain embodiments of the invention, the composition is free of wax.

Dyestuffs

The compositions in accordance with the invention may comprise at least one dyestuff.

This (or these) dyestuff(s) are preferably chosen from pulverulent substances, liposoluble dyes and water-soluble dyes, and mixtures thereof.

Preferably, the compositions according to the invention comprise at least one pulverulent dyestuff. The pulverulent dyestuffs may be chosen from pigments and nacres, and preferably from pigments.

The pigments may be white or coloured, mineral and/or organic, and coated or uncoated. Among the mineral pigments, mention may be made of metal oxides, in particular titanium dioxide, optionally surface-treated, zirconium, zinc or cerium oxide, and also iron, titanium or chromium oxide, manganese violet, ultramarine blue, chromium hydrate and ferric blue. Among the organic pigments that may be mentioned are carbon black, pigments of D&C type and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with in particular ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

Preferably, the pigments contained in the compositions according to the invention are chosen from metal oxides.

More preferably, the pigments contained in the compositions of mascara type are chosen from iron oxides, such as especially those sold under the name Sunpuro Black Iron Oxide 033-7001® by the company SunChemical.

These dyestuffs may be present in a content ranging from 0.2% to 40% by weight and more particularly from 0.5% to 22% by weight, relative to the total weight of the composition. According to a more particular variant of the invention, the content of dyestuffs represents from 0.8% to 15% by weight relative to the total weight of the composition.

Fibres

The composition according to the invention may also comprise at least one fibre.

The term "fibre" should be understood as meaning an object of length L and of diameter D such that L is greater than D and preferably very much greater than D, D being the diameter of the circle in which the cross section of the fibre is inscribed. In particular, the ratio L/D (or aspect ratio) is chosen in the range from 3.5 to 2,500, preferably from 5 to 500 and better still from 5 to 150.

The fibres that may be used in the composition of the invention may be mineral or organic fibres, of synthetic or natural origin. They may be short or long, individual or organized, for example braided, and hollow or solid. They may have any shape and may especially have a circular or polygonal (square, hexagonal or octagonal) cross section depending on the specific application envisaged. In particular, their ends are blunted and/or polished to prevent injury.

In particular, the fibres have a length ranging from 1 µm to 10 mm, preferably from 0.1 mm to 5 mm and better still from 0.3 mm to 3 mm. They may have a cross section included within a circle with a diameter ranging from 2 nm to 500 µm, preferably ranging from 100 nm to 100 µm and better still from 1 µm to 50 µm. The weight or yarn count of fibres is often given in denier or decitex and represents the weight in grams per 9 km of yarn. Preferably, the fibres according to the invention have a yarn count chosen in the range from 0.01 to 10 denier, preferably from 0.1 to 2 denier and better still from 0.3 to 0.7 denier.

The fibres that may be used in the compositions according to the invention may be chosen from rigid or non-rigid fibres, and may be of synthetic or natural, mineral or organic origin.

Moreover, the fibres may or may not be surface-treated, may be coated or uncoated, and may be coloured or uncoloured.

As fibres that may be used in the compositions according to the invention, mention may be made of non-rigid fibres such as polyamide (Nylon®) fibres or rigid fibres such as polyimideamide fibres, for instance those sold under the names Kermel® and Kermel Tech® by the company Rhodia or poly(p-phenyleneterephthalamide) (or aramid) fibres sold especially under the name Kevlar® by the company DuPont de Nemours.

The fibres may be present in a content ranging from 0.1% to 30% by weight, more particularly from 0.1% to 25% by weight and preferably from 0.3% to 10% by weight relative to the weight of the composition. In accordance with a first embodiment, the content of fibres, if they are present, ranges from 2% to 25% by weight, relative to the weight of the composition. In accordance with another preferred embodiment of the invention, the content of fibres, if they are present, is less than or equal to 10% by weight and preferably less than or equal to 5% by weight, relative to the weight of the composition.

Additional Fillers

The term "fillers" should be understood as meaning colourless or white solid particles of any form, which are in a form that is insoluble and dispersed in the medium of the composition, and are of mineral or organic nature.

In the present patent application, "mineral filler" is understood to mean any mineral solid that is insoluble in the medium at room temperature (25° C.).

The term "mineral" refers to any compound or polymer whose chemical structure does not comprise any carbon atoms.

The fillers may or may not be surface-coated, and in particular they may be surface-treated with silicones, amino acids, fluoro derivatives or any other substance that promotes the dispersion and compatibility of the filler in the composition.

Such fillers are distinct from the mineral thickeners and also from the colouring agents described previously.

The fillers may be spherical, i.e. they may comprise at least a rounded general portion, preferably defining at least a sphere portion, preferably internally defining a concavity or a hollow (sphere, globules, bowls, horseshoe, and the like), or lamellar.

Such fillers are advantageously chosen from:

silica powders, such as the porous silica microspheres sold under the name Silica Beads SB-700 by the company Miyoshi or Sunsphere® H51 or Sunsphere® H33 by the company Asahi Glass; or the polydimethylsiloxane-coated amorphous silica microspheres sold under the name SA Sunsphere® H33 or SA Sunsphere® H-53 by the company Asahi Glass, acrylic (co)polymers powders and derivatives thereof, in particular:

the polymethyl methacrylate powder sold under the names Covabead® LH85 by the company Wackherr or Microsphere M-100® by the company Matsumoto, the polymethyl methacrylate/ethylene glycol dimethacrylate powder sold under the name Dow Corning 5640 Microsponge® Skin Oil Adsorber by the company Dow Corning or Ganzpearl® GMP-0820 by the company Ganz Chemical, the polyallyl methacrylate/ethylene glycol dimethacrylate powder sold under the name Poly-Pore® L200 or Poly-Pore® E200 by the company Amcol Health and Beauty Solutions Inc., the ethylene glycol dimethacrylate/lauryl methacrylate copolymer powder sold under the name Polytrap® 6603 by the company Dow Corning, optionally crosslinked acrylate/alkyl acrylate copolymer powder crosslinked acrylate/ethylhexyl acrylate copolymer powder sold under the name Techpolymer ACP-8C by the company Sekisui Plastics, ethylene/acrylate copolymer powder, such as the product sold under the name Flobeads® by the company Sumitomo Seika Chemicals, the expanded hollow particles of acrylonitrile (co) polymer sold under the name Expancel by Expancel or the microspheres sold under the name Micropearl F 80 ED® by the company Matsumoto, the polyurethane powders sold, for example, under the names Plastic Powder D-400, Plastic Powder CS-400, Plastic Powder D-800 and Plastic Powder T-75 by the company Toshiki, silicone powders advantageously chosen from:
- polymethylsilsesquioxane powders, in particular those sold under the name Tospearl, in particular Tospearl 145 A, by the company Momentive Performance Materials,
- organopolysiloxane elastomer powders coated with silicone resin, especially with silsesquioxane resin, such as the products sold under the name KSP-100, KSP-101, KSP-102, KSP-103, KSP-104 or KSP-105 by the company Shin-Etsu (INCI name: vinyl dimethicone/methicone silsesquioxane crosspolymer),
- silicone elastomer powders, such as the products sold under the name Trefil® Powder E-505C or Trefil® Powder E-506C by the company Dow Corning,
- powders of organosilicone particles, for example, in the form of bowls, such as those described in JP-2003 128 788 or JP-A-2000-191789 or also in patent application EP 1 579 841 and sold especially by the company Takemoto Oil & Fat, polyamide powders, such as Nylon® powders, in particular Nylon 12 powders, such as the nylon powders sold under the name Orgasol® 2002 EXS NAT COS by the company Arkema, powders of natural organic materials, such as polysaccharide powders and in particular starch powders, especially crosslinked or non-crosslinked corn, wheat or rice starch powders, powders of starch crosslinked with octenylsuccinic anhydride sold under the name Dry-Flo® by the company National Starch or powders of waxy corn starch, such as those which are sold under the names C* Gel 04201 by the company Cargill, Corn Starch B by the company Roquette and Organic Corn Starch by the company Draco Natural Products, spherical cellulose microparticles, such as Cellulobeads D-10, Cellulobeads D-5 and Cellulobeads USF, sold by the company Daito Kasei Kogyo, particles of N—($C_8$-$C_{22}$ carbon atoms acylated) amino acids; the amino acid may be, for example, lysine, glutamic acid or alanine, preferably lysine, for example Amihope LL by the company Ajinomoto or the product sold under the name Corum 5105 S by the company Corum, Perlite powders, such as those sold by the company World Minerals under the trade name Perlite P1430, Perlite P2550, Perlite P2040 or OpTiMat™ 1430 OR or 2550 OR. Europerl EMP-2 and Europerl 1 by the company Imerys, zeolites, such as the products sold by the company Zeochem under the names Zeoflair 300, Zeoflair 200, Zeoflair 100, X-Mol and X-Mol MT, calcium magnesium carbonate particles, such as those sold by the company Imerys under the name Calcidol, by the company LCW (Sensient) under the name Carbomat or by the company Omya under the name Omyacare 60-AV.

Use may also be made of talc particles, for example sold under the names Luzenac Pharma M and UM by the company Imerys and Rose Talc and Talc SG-2000 by the company Nippon Talc; natural or synthetic mica particles, such as those sold under the names Mica M RP and Silk Mica by the company Merck, or the product sold under the name Sericite S-152-BC by the company Miyoshi Kasei; calcium carbonate and magnesium hydrogen carbonate; hydroxyapatite; boron nitride; fluorphlogopite; and mixtures thereof.

The spherical fillers may be coated with a hydrophobic treatment agent. The hydrophobic treatment agent may be chosen from fatty acids, for instance stearic acid; metal soaps, for instance aluminium dimyristate, the aluminium salt of hydrogenated tallow glutamate; amino acids; N-acylamino acids or salts thereof; lecithin, isopropyl triisostearyl titanate, and mixtures thereof. The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be the aluminium, magnesium, calcium, zirconium, zinc, sodium or potassium salts. The amino acid may be, for example, lysine, glutamic acid or alanine. The term "alkyl" mentioned in the compounds cited above especially denotes an alkyl group containing from 1 to 30 carbon atoms and preferably containing from 5 to 16 carbon atoms.

The composition advantageously has a content of additional filler(s) of between 0.5% and 30% by weight, more particularly from 2% to 15% by weight and preferably from 2% to 15% by weight, relative to the weight of the composition.

According to certain embodiments, the content of additional filler(s) is less than or equal to 10% by weight and preferably less than or equal to 5% by weight, relative to the weight of the composition. Preferably, the composition is free of fillers.

Optional Additives

The composition may comprise at least one optional ingredient chosen, for example, from film-forming agents other than the stabilized polymer particles described previously; antioxidants; preserving agents; fragrances; flavourings; neutralizers; emollients; organic thickeners; coalescers; moisturizers; vitamins, and mixtures thereof.

According to one embodiment of the invention, the composition comprises at least one plasticizer. In the case where the polymer particles are provided in the form of a dispersion, the plasticizer is then advantageously present in said oily dispersion.

The plasticizers may be chosen from tri-n-butyl citrate, tripropylene glycol monomethyl ether (INCI name: PPG-3 methyl ether) and trimethyl pentaphenyl trisiloxane (sold under the name Dow Corning PH-1555 HRI Cosmetic Fluid by the company Dow Corning). These plasticizers make it possible to improve the mechanical strength of the polymer film.

The plasticizer may be present in a content ranging from 1 to 50% by weight, advantageously from 2% to 50% by weight, preferably from 2% to 40% by weight and even more particularly less than 20% by weight, relative to the weight of the composition.

Needless to say, a person skilled in the art will take care to select the optional additional additives and/or the amount thereof such that the advantageous properties of the composition according to the invention are not, or are not substantially, adversely affected by the envisaged addition.

The compositions according to the invention are thus intended for caring for and/or making up keratin materials, in particular the skin or the lips, and also keratin fibres especially such as the eyelashes or the eyebrows.

They advantageously contain a physiologically acceptable medium, in other words a medium that is compatible with the treated keratin materials.

The compositions according to the invention may be in fluid or solid form, or alternatively in optionally compacted powder form. Preferably, the compositions are in fluid form.

The term "fluid" refers to compositions for which it is possible to measure the viscosity at 25° C. and atmospheric pressure ($1.013 \times 10^5$ Pa).

The compositions according to the invention may also be in anhydrous form, or in the form of oil-in-water or water-in-oil emulsions.

If the compositions comprise water, the water content advantageously does not exceed 15% by weight and even more particularly does not exceed 10% by weight relative to the weight of the composition. Preferably, if it is present, the water content does not exceed 5% by weight relative to the weight of the composition, and advantageously does not exceed 2% by weight, relative to the weight of the composition.

In accordance with a preferred embodiment of the invention, the compositions are anhydrous.

The term "anhydrous" means that water is not deliberately added to the compositions, but may be present in trace amount in the various compounds used in the compositions.

Advantageously, the composition according to the invention is a makeup composition, in particular a mascara, an eyeliner, an eyeshadow, a foundation or a lipstick which is in solid or fluid form.

Preferably, the hydrocarbon-based oil of the composition is chosen from volatile oils.

Needless to say, these compositions are advantageously pigmented. Reference may be made to the description as regards the nature and content of these compounds.

As regards mascaras and eyeliners, these compositions conventionally have a viscosity at 25° C. and atmospheric pressure ($1.1013 \times 10^5$ Pa) of from 0.1 to 50 Pa·s, in particular from 1 to 30 Pa·s. In the case of mascaras, the viscosity is more particularly greater than or equal to 4 Pa·s (measured with a Rheomat RM100®).

Advantageously, if these composition comprise at least one non-volatile oil, the content of these non-volatile oil(s) remains less than 5% by weight relative to the weight of the composition. In accordance with an even more preferred embodiment, these compositions are free of non-volatile oil(s).

The compositions of mascara type may also comprise at least one wax. The content of these compound(s) is determined by a person skilled in the art as a function of the content of mineral thickener present in the composition and of the viscosity desired for the same.

According to a particular embodiment of the invention, the compositions of eyeliner type have a content of additional filler(s) of less than 5% by weight, more particularly less than 2% by weight and even more preferentially less than 1% by weight, relative to the weight of the composition. Even more particularly, the composition according to this variant is free of said filler(s).

As regards foundations, the present invention more particularly concerns compositions whose viscosity ranges between 0.04 and 2 Pa·s (measured with a Rheomat RM 180 viscometer from Mettler (thermostatically set at 25° C. and $1.013 \times 10^5$ Pa).

Preferably, these compositions comprise at least one additional filler, advantageously in a content of between 0.5% and 30% by weight and more particularly between 2% and 15% by weight, relative to the weight of the composition.

As regards lip makeup compositions, they may be in a solid form (wand, dish) or in a fluid form (gloss) and preferably in fluid form.

In addition to the surface-stabilized polymer particles and the mineral thickener, the compositions may comprise waxes, the content of which may be adjusted as a function of the desired galenical form (solid or fluid). Usually, the viscosity of fluid lipstick compositions ranges from 0.3 Pa·s to 3 Pa·s.

Preferably, said compositions comprise at least one plasticizer as described previously.

The invention is illustrated in more detail in the following examples.

All the percentages of reagents described in the examples are weight percentages.

EXAMPLES

Synthesis Examples

Example 1

In a first step, 1300 g of isododecane, 337 g of isobornyl acrylate, 28 g of methyl acrylate and 3.64 g of tert-butyl peroxy-2-ethylhexanoate (Trigonox 21S from Akzo) were placed in a reactor. The isobornyl acrylate/methyl acrylate mass ratio is 92/8. The mixture was heated at 90° C. under argon with stirring.

After 2 hours of reaction, 1430 g of isododecane were added to the reactor feedstock and the mixture was heated to 90° C.

In a second step, a mixture of 1376 g of methyl acrylate, 1376 g of isododecane and 13.75 g of Trigonox 21S were run in over 2 hours 30 minutes, and the mixture was left to react for 7 hours. 3.3 litres of isododecane were then added and part of the isododecane was evaporated off to obtain a solids content of 50% by weight.

A dispersion of methyl acrylate particles stabilized with a statistical copolymer stabilizer containing 92% isobornyl acrylate and 8% methyl acrylate in isododecane was obtained.

The oily dispersion contains in total (stabilizer+particles) 80% methyl acrylate and 20% isobornyl acrylate.

The polymer particles of the dispersion have a number-average size of about 160 nm.

The dispersion is stable after storage for 7 days at room temperature (25° C.).

Example 2

A dispersion of polymer in isododecane was prepared according to the preparation method of Example 1, using:

Step 1: 275.5 g of isobornyl acrylate, 11.6 g of methyl acrylate, 11.6 g of ethyl acrylate, 2.99 g of Trigonox 21, 750 g of isododecane; followed by addition, after reaction, of 750 g of isododecane.

Step 2: 539.5 g of methyl acrylate, 539.5 g of ethyl acrylate, 10.8 g of Trigonox 21S, 1079 g of isododecane. After reaction, addition of 2 litres of isododecane and evaporation to obtain a solids content of 35% by weight.

A dispersion in isododecane of methyl acrylate/ethyl acrylate (50/50) copolymer particles stabilized with an isobornyl acrylate/methyl acrylate/ethyl acrylate (92/4/4) statistical copolymer stabilizer was obtained.

The oily dispersion contains in total (stabilizer+particles) 40% methyl acrylate, 40% ethyl acrylate and 20% isobornyl acrylate.

The dispersion is stable after storage for 7 days at room temperature (25° C.).

Example 3

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 303 g of methyl acrylate, 776 g of ethyl acrylate, 157 g of acrylic acid, 11 g of Trigonox 21S, 741.6 g of isododecane and 494.4 g of ethyl acetate. After reaction, addition of 3 litres of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (24.5/62.8/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 20% methyl acrylate, 50% ethyl acrylate and 20% isobornyl acrylate.

The dispersion is stable after storage for 7 days at room temperature (25° C.).

Example 4

A dispersion of polymer in isododecane was prepared according to the preparation method of Example 1, using:

Step 1: 315.2 g of isobornyl acrylate, 12.5 g of methyl acrylate, 12.5 g of ethyl acrylate, 3.4 g of Trigonox 21, 540 g of isododecane, 360 g of ethyl acetate; followed by addition, after reaction, of 540 g of isododecane and 360 g of ethyl acetate.

Step 2: 145 g of methyl acrylate, 934 g of ethyl acrylate, 157 g of acrylic acid, 12.36 g of Trigonox 21S, 741.6 g of isododecane and 494.4 g of ethyl acetate. After reaction, addition of 3 litres of an isododecane/ethyl acetate mixture (60/40 weight/weight) and total evaporation of the ethyl acetate and partial evaporation of the isododecane to obtain a solids content of 44% by weight.

A dispersion in isododecane of methyl acrylate/ethyl acrylate/acrylic acid (11.7/75.6/12.7) copolymer particles stabilized with an isobornyl acrylate/methyl acrylate/ethyl acrylate (92/4/4) statistical copolymer stabilizer was obtained.

The oily dispersion contains in total (stabilizer+particles) 10% acrylic acid, 10% methyl acrylate, 60% ethyl acrylate and 20% isobornyl acrylate.

The dispersion is stable after storage for 7 days at room temperature (25° C.).

Example 5

A dispersion of polymer in isododecane was prepared according to the preparation method of Example 1, using:

Step 1: 48 g of isobornyl acrylate, 2 g of methyl acrylate, 2 g of ethyl acrylate, 0.52 g of Trigonox 21, 57.6 g of isododecane, 38.4 g of ethyl acetate; followed by addition, after reaction, of 540 g of isododecane and 360 g of ethyl acetate.

Step 2: 98 g of methyl acrylate, 73 g of ethyl acrylate, 25 g of maleic anhydride, 1.96 g of Trigonox 21S, 50.4 g of isododecane and 33.60 g of ethyl acetate. After reaction, addition of 1 litre of an isododecane/ethyl acetate mixture (60/40 weight/weight) and total evaporation of the ethyl acetate and partial evaporation of the isododecane to obtain a solids content of 46.2% by weight.

A dispersion in isododecane of methyl acrylate/ethyl acrylate/maleic anhydride (50/37.2/12.8) copolymer particles stabilized with an isobornyl acrylate/methyl acrylate/ethyl acrylate (92/4/4) statistical copolymer stabilizer was obtained.

The oily dispersion contains in total (stabilizer+particles) 10% maleic anhydride, 30% methyl acrylate, 40% ethyl acrylate and 20% isobornyl acrylate.

The dispersion is stable after storage for 7 days at room temperature (25° C.).

Example 6

A dispersion of polymer in isododecane was prepared according to the preparation method of Example 1, using:

Step 1: 48.5 g of isobornyl methacrylate, 4 g of methyl acrylate, 0.52 g Trigonox 21, 115 g of isododecane; followed by addition, after reaction, of 80 g of isododecane.

Step 2: 190 g of methyl acrylate, 1.9 g of Trigonox 21S, 190 g of isododecane. After reaction, addition of 1 litre of isododecane and partial evaporation of the isododecane to obtain a solids content of 48% by weight.

A dispersion in isododecane of methyl acrylate polymer particles stabilized with an isobornyl methacrylate/methyl acrylate (92/8) statistical copolymer stabilizer was obtained.

The oily dispersion contains in total (stabilizer+particles) 80% methyl acrylate and 20% isobornyl methacrylate.

The dispersion is stable after storage for 7 days at room temperature (25° C.).

Examples 7 and 8 (Invention) and 9 and 10 (Outside the Invention)

Several oily dispersions of polymethyl acrylate stabilized with a stabilizer containing isobornyl acrylate and optionally methyl acrylate were prepared, according to the procedure of Example 1, by varying the mass ratio of isobornyl acrylate and methyl acrylate and observing the stability of the dispersion obtained as a function of the chemical constitution of the stabilizer.

All the dispersions comprise in total (stabilizer+particles) 80% methyl acrylate and 20% isobornyl acrylate.

Example 7

Step 1: 50 g of isobornyl acrylate, 0.5 g Trigonox 21, 96 g of isododecane; followed by addition, after reaction, of 80 g of isododecane.

Step 2: 200 g of methyl acrylate, 2 g of Trigonox 21S, 200 g of isododecane. After reaction, addition of 80 g of isododecane and evaporation to obtain a solids content of 31% by weight.

A dispersion in isododecane of polymethyl acrylate particles stabilized with a polyisobornyl acrylate stabilizer was obtained.

Example 8

Step 1: 48.5 g of isobornyl acrylate, 8.5 g of methyl acrylate, 0.57 g Trigonox 21, 115 g of isododecane; followed by addition, after reaction, of 75 g of isododecane.

Step 2: 185.5 g of methyl acrylate, 1.85 g of Trigonox 21S, 185.5 g of isododecane. After reaction, addition of 75 g of isododecane and evaporation to obtain a solids content of 31% by weight.

A dispersion in isododecane of polymethyl acrylate particles stabilized with an isobornyl acrylate/methyl acrylate (85/15) statistical copolymer stabilizer was obtained.

Example 9 (Outside the Invention)

Step 1: 48.5 g of isobornyl acrylate, 12 g of methyl acrylate, 0.6 g Trigonox 21, 115 g of isododecane; followed by addition, after reaction, of 60 g of isododecane.

Step 2: 182 g of methyl acrylate, 1.82 g of Trigonox 21S, 182 g of isododecane. After reaction, addition of 60 g of isododecane and evaporation to obtain a solids content of 31% by weight.

A dispersion in isododecane of polymethyl acrylate particles stabilized with an isobornyl acrylate/methyl acrylate (80/20) statistical copolymer stabilizer was obtained.

Example 10 (Outside the Invention)

Step 1: 48.5 g of isobornyl acrylate, 21 g of methyl acrylate, 0.7 g Trigonox 21, 130 g of isododecane; followed by addition, after reaction, of 65 g of isododecane.

Step 2: 173 g of methyl acrylate, 1.73 g of Trigonox 21S, 173 g of isododecane. After reaction, addition of 65 g of isododecane and evaporation to obtain a solids content of 31% by weight.

A dispersion in isododecane of polymethyl acrylate particles stabilized with an isobornyl acrylate/methyl acrylate (70/30) statistical copolymer stabilizer was obtained.

The stability 12 hours after the end of synthesis of the oily dispersions of polymethyl acrylate of Examples 1 and 7 to 10 was compared, and the following results were obtained.

| Example | Stabilizer | Stability |
|---|---|---|
| 1 | 92 isobornyl acrylate/ 8 methyl acrylate | Stable |
| 7 | 100 isobornyl acrylate | Stable |
| 8 | 85 isobornyl acrylate/ 15 methyl acrylate | Stable |
| 9 | 80 isobornyl acrylate/ 20 methyl acrylate | Phase separation and setting to a solid |
| 10 | 70 isobornyl acrylate/ 30 methyl acrylate | Phase separation and setting to a solid |

The results obtained show that the dispersions of polymethyl acrylate in isododecane are stable when the stabilizer is an isobornyl acrylate homopolymer or an isobornyl acrylate/methyl acrylate copolymer with an isobornyl acrylate/methyl acrylate weight ratio >80/20.

Moreover, the film obtained with the oily dispersions of Examples 1, 7 and 8 have the following properties:

| Gloss at 20° | Resistance to fatty substances | Tacky |
|---|---|---|
| 72 | Resistant to fatty substances | Non-tacky |
| 69 | Resistant to fatty substances | Non-tacky |
| 65 | Resistant to fatty substances | Non-tacky |

Examples 11 and 12 (Outside the Invention)

Tests were performed with other monomers bearing a cyclic group by replacing the isobornyl acrylate, performing step 1 of Example 1, i.e. preparing a cyclic monomer/methyl acrylate (92/8) statistical copolymer stabilizer. All the stabilizers prepared in isododecane led to a medium that set to a solid in the form of a viscous precipitate. This shows that such stabilizers are unsuitable for forming an oily dispersion since they are incompatible with isododecane, in contrast with the stabilizers prepared in Examples 1 to 8 described previously.

| Examples | Stabilizer | Compatibility in isododecane |
|---|---|---|
| 11 | Cyclohexyl acrylate/methyl acrylate (92/8) | Incompatible (viscous precipitate) |
| 12 | Cyclohexyl methacrylate/methyl acrylate (92/8) | Incompatible (viscous precipitate) |

Examples 13: Mascara

The following compositions, the ingredients of which are given in the table below, are prepared. Compositions 1 to 3 are in accordance with the invention; compositions A and B are compositions outside the invention.

The amounts are indicated by weight of starting materials.

| | Ingredients | 1 | 2 | 3 | A | B |
|---|---|---|---|---|---|---|
| A | Carnauba wax (Cerauba T1; Baerlocher) | 5 | — | — | 5 | — |
| | Paraffin wax (Affine 56-58 Pastilles; Baerlocher) | 10 | — | — | 10 | — |
| B | Isododecane (Ineos) | 54.5 | 72 | 37 | 72 | 42 |
| | Disteardimonium hectorite (Bentone 38 VCG; Elementis) | 2 | 4 | 4 | 4 | — |
| | Propylene carbonate (Huntsman) | 0.5 | 1 | 1 | 1 | — |
| | Copolymer (methyl acrylate)-co-(isobornyl acrylate)) in isododecane (according to Example 1) | 20 | 15 | 50 | — | 50 |
| C | Iron oxide (Sunpuro C33-7001, Sun) | 7 | 7 | 7 | 7 | 7 |
| D | Preserving agent | 1 | 1 | 1 | 1 | 1 |

Protocol for Preparing the Compositions

Preparation of Phase a (Comprising the Waxes) for Compositions 1 and A

The waxes are melted in a heating pan (95-98° C.).

Preparation of Phase B

Phase B is prepared at 70° C. with stirring for 30 minutes using a Rayneri blender. For compositions 1 and A, after phase A has totally melted, phase B is poured into phase A with stirring for 30 minutes.

Addition of Phase C

Phase C is introduced into phase A+B for compositions 1 and A or into phase B for compositions 2, 3 and B.

Stirring is continued for 10 minutes.

The preparation is cooled to room temperature.

Addition of Phase D

Phase D is introduced at room temperature into the resulting mixture with stirring until a homogeneous preparation is obtained.

Each of the mascara compositions thus obtained is transferred into a closed container to prevent it from drying out on contact with air.

After 24 hours at room temperature, the satisfactory homogeneity and dispersion of the pigment are evaluated.

Evaluation of the Viscosity:

RM 100 Rheomat viscometer from Mettler (at 25° C. and $1.013 \times 10^5$ Pa).

The texture is acceptable if the measured viscosity is greater than 4 Pa·s.

Makeup-Removal Evaluation

Removal of makeup using cotton wool and a makeup-removing composition Bi-Facil from Lancôme. The makeup removal is acceptable if the mascara is removed as cohesive sheaths and does not leave any blackish marks on the cotton wool and around the eyes.

| Compositions | 1 | 2 | 3 | A | B |
|---|---|---|---|---|---|
| Viscosity (Pa · s) | 14.5 | 17.5 | 19.6 | 13.2 | 1 |
| makeup removal | as sheath | as sheath | as sheath | black mark | as sheath |

It is thus found that only the compositions according to the invention have a suitable texture and can be removed without leaving any black marks.

The same results are obtained by replacing the dispersion of copolymer of Example 1 with the same amount as that of Example 4.

Examples 14: Mascara

The following compositions, the ingredients of which are given in the table below, are prepared. Compositions 4 and 5 are in accordance with the invention; composition C is a composition outside the invention.

The amounts are indicated as weight of starting materials.

| | Ingredients | 4 | 5 | C |
|---|---|---|---|---|
| A | Carnauba wax (Cerauba T1; Baerlocher) | 5 | — | — |
| | Paraffin wax (Affine 56-58 Pastilles; Baerlocher) | 10 | — | — |
| B | Isododecane (Ineos) | 52 | 27 | 42 |
| | Silica silylate (Aerogel VM-2270; Dow Corning) | 5 | 15 | — |
| | Copolymer (methyl acrylate)-co-(isobornyl acrylate)) in isododecane (according to Example 1) | 20 | 50 | 50 |
| C | Iron oxide (Sunpuro C33-7001, Sun) | 7 | 7 | 7 |
| D | Preserving agent | 1 | 1 | 1 |

Protocol for Preparing the Compositions
Preparation of Phase A of Composition 4
The waxes are melted in a heating pan (95-98° C.).
Preparation of Phase B
Phase B is prepared at 70° C. with stirring for 30 minutes using a Rayneri blender. For composition 4, after phase A has totally melted, phase B is poured into phase A with stirring for 30 minutes.
Addition of Phase C
Phase C is introduced into phase A+B for composition 4 or into phase B for compositions 5 and C.
Stirring is continued for 10 minutes.
The preparation is cooled to room temperature.
Addition of Phase D
Phase D is introduced at room temperature into the resulting mixture with stirring until a homogeneous preparation is obtained.

Each of the mascara compositions thus obtained is transferred into a closed container to prevent it from drying out on contact with air.

After 24 hours at room temperature, the satisfactory homogeneity and dispersion of the pigment are evaluated.
Results:

The viscosity and the makeup removal were evaluated under the conditions detailed in the preceding mascara example.

| Compositions | 4 | 5 | C |
|---|---|---|---|
| Viscosity (Pa · s) | 16.6 | 12.1 | 1 |
| makeup removal | as sheath | as sheath | as sheath |

Tests 4 and 5 are repeated, replacing the dispersion of copolymer of Example 1 with the same amount as that of Example 4, and give the same results.

Examples 15: Foundation

The following compositions, the ingredients of which are given in the table below, are prepared.

Composition 6 is in accordance with the invention; composition D is outside the invention.

The amounts are indicated as weight of starting materials.

| Ingredients | 6 | D |
|---|---|---|
| Copolymer (methyl acrylate)-co-(isobornyl acrylate)) in isododecane (according to Example 1) | 51.16 | — |
| Polypropylsilsesquioxane in isododecane (Dow Corning 680 ID Fluid; Dow Corning) (75% AM) | — | 34.99 |
| Iron oxides (and) disodium stearoyl glutamate (and) aluminium hydroxide, (yellow) from Miyoshi Kasei | 1.58 | 1.58 |
| Iron oxides (and) disodium stearoyl glutamate (and) aluminium hydroxide, (red) from Miyoshi Kasei | 0.41 | 0.41 |
| Iron oxides (and) disodium stearoyl glutamate (and) aluminium hydroxide, (black) from Miyoshi Kasei | 0.15 | 0.15 |
| Titanium dioxide (and) disodium stearoyl glutamate (and) aluminium hydroxide, (white) from Miyoshi Kasei | 8.66 | 8.66 |
| Mica (Synafil S 1050 from Eckart) | 1.20 | 1.20 |
| Disteardimonium hectorite (Bentone Gel ISD V, with propylene carbonate, isododecane; 10% active material) | 30 | 30 |
| Isododecane | 6.84 | 23.01 |

Protocol for Preparing the Compositions:

The required amounts of copolymer are first mixed with the isododecane, with stirring using a Rayneri blender, at room temperature.

Once the mixture has been homogenized, the pigments are added with stirring and this mixture is homogenized for 10 minutes.

The mixture comprising the disteardimonium hectorite is finally added and the whole is mixed until a homogeneous composition is obtained.
Evaluation of the Compositions and Results:

The composition according to the invention is much thicker than the comparative composition.

They are both stable at 24 hours at room temperature and after 4 weeks at room temperature.

The composition according to the invention does not leave any transfer marks, when dry or in the presence of sebum.

In the case of the comparative composition, it is not possible to perform the tests under the normal conditions: the specimens are tacky and the comparative composition consequently leaves many marks.

Examples 16: Lipsticks

The following compositions, the ingredients of which are collated in the table below, are prepared.

The amounts are indicated as weight of starting materials, unless otherwise indicated.

|  | 7 | 8 | 9 | 10 |
|---|---|---|---|---|
| Copolymer (methyl acrylate)-co-(ethyl acrylate)-co-(isobornyl acrylate) in isododecane according to Example 2 | 60 | 60 | 70 | 60 |
| Disteardimonium hectorite (Bentone Gel ISD V, with propylene carbonate, isododecane; Elementis) (amount expressed as active material) | 0 | 0.5 | 0 | 1 |
| Silica silylate (Aerogel VM-2270; Dow Corning) | 1.4 | 2.6 | 3.8 | 3.8 |
| Trimethyl siloxysilicate (SR1000 from Momentive Performance Materials) | 5 | 5 | 5 | 5 |
| C30-45 Alkyldimethylsilyl polypropylsilsesquioxane (Dow Corning SW-8005 C30 Resin Wax from Dow Corning) | 2.5 | 0.5 | 2.5 | 2.5 |
| Tributyl citrate | 0 | 0 | 0 | 1 |
| Red 7 pigment | 4.8 | 4.8 | 4.8 | 4.8 |
| Isododecane | qs | qs | qs | qs |

Protocol for Preparing the Compositions

The polymer dispersion is mixed with the mineral thickener in a heating pan and the mixture is homogenized at room temperature using a Rayneri blender.

The silicone resin (trimethyl siloxysilicate) is then added, followed by the wax predissolved at 60° C. in part of the isododecane.

A mixture of the pigment with part of the isododecane and the plasticizer (tributyl citrate), when it is present in the formula, is prepared separately by treating in a three-roll machine, and is added to the preceding mixture.

The mixture is homogenized with the Rayneri blender for 20 minutes, so as to obtain a smooth, homogeneous mixture.

The composition is completed by adding the amount of isododecane evaporated during the manufacture.

Evaluation of the Compositions:
Oil Resistance Test:

The composition is applied to a Bioskin skin sample (25 μm thickness of the wet film).

The sample is left to dry for 24 hours at 35° C.

After the drying step, a drop of olive oil is placed on the film of composition and left for 10 minutes.

The oil is then wiped five times using cotton wool.

The integrity of the film after wiping with the cotton wool is observed to evaluate the oil resistance of the composition, on a scale ranging from 1 to 3 (1: excellent resistance, 2: intermediate resistance, and 3: poor resistance).

Results:

The compositions according to the invention apply easily and homogeneously, as a non-tacky deposit. Moreover, the compositions according to the invention all show excellent oil resistance.

Examples 17: Lipsticks

The following compositions, the ingredients of which are collated in the table below, are prepared.

The amounts are indicated as weight of starting materials, unless otherwise indicated.

|  | 11 | 12 | 13 |
|---|---|---|---|
| Copolymer (methyl acrylate)-co-(ethyl acrylate)-co-(acrylic acid)-co-(isobornyl acrylate) in isododecane according to Example 4 | 64.7 | 64.7 | — |
| Copolymer (methyl acrylate)-co-(ethyl acrylate)-co-(acrylic acid)-co-(acrylic acid)-co-(isobornyl acrylate) in isododecane according to Example 3 | — | — | 70 |
| Disteardimonium hectorite (Bentone Gel ISD V, with propylene carbonate, isododecane; Elementis) (% active material) | 1.5 | — | — |
| Silica silylate (Aerogel VM-2270; Dow Corning) | — | 3.81 | 3.81 |
| Trimethyl siloxysilicate (SR1000 from Momentive Performance Materials) | — | 2.5 | 2.5 |
| C30-45 Alkyldimethylsilyl polypropylsilsesquioxane (Dow Corning SW-8005 C30 Resin Wax from Dow Corning) | 0.6 | 2.5 | 2.5 |
| Tributyl citrate | 2.8 | 2.8 | 2.9 |
| Red 7 pigment | 1 | 1 |  |
| Isododecane | qs | qs | qs |

The preparation protocol is similar to that of the preceding example.

Evaluation of the Compositions
Oil Resistance Test:

The test was detailed in the preceding example.

Transfer Test

The composition is applied to a Bioskin skin sample (25 μm thickness of the wet film).

The sample is left to dry for 24 hours at 35° C.

After the drying step, a piece of adhesive tape is applied to the film of composition and removed at an angle of 180°.

The integrity of the film is observed after removing the adhesive tape and the transfer resistance is evaluated on a scale ranging from 1 to 3 (1: no peeling, 2: partial peeling, and 3: total peeling).

|  | 11 | 12 | 13 |
|---|---|---|---|
| Transfer test | 1 | 1 | 1 |
| Oil resistance | 1 | 1 | 1 |

The invention claimed is:

1. A composition, comprising:
   particles of at least one polymer that is surface-stabilized with a stabilizer;
   at least one hydrocarbon-based oil; and
   at least one mineral thickener selected from the group consisting of optionally modified clays, optionally modified silicas, and mixtures thereof,
   wherein
   the polymer of the panicles comprises a $C_1$-$C_4$ alkyl (meth)acrylate polymer;
   the stabilizer comprises an isobornyl (meth)acrylate polymer selected from the group consisting of a isobornyl (meth)acrylate homopolymer and a statistical copolymer of isobornyl (meth)acrylate and of a $C_1$-$C_4$ alkyl (meth)acrylate, and
   an isobornyl (meth)acrylate/$C_1$-$C_4$ alkyl (meth)acrylate weight ratio is greater than 4.

2. The composition according to claim 1, wherein the polymer of the particles comprises at least one of methyl acrylate and ethyl acrylate polymer.

3. The composition according to claim 1, wherein the polymer of the particles comprises an ethylenically unsaturated acid monomer or the anhydride thereof.

4. The composition according to claim 1, wherein the polymer of the particles comprises from 80% to 100% by weight of a $C_1$-$C_4$ alkyl (meth)acrylate and from 0 to 20% by weight of an ethylenically unsaturated acid monomer, relative to the total weight of the polymer.

5. The composition according to claim 1, wherein the polymer of the particles is selected from the group consisting of:
methyl acrylate homopolymers,
ethyl acrylate homopolymers,
methyl acrylate/ethyl acrylate copolymers,
methyl acrylate/ethyl acrylate/acrylic acid copolymers,
methyl acrylate/ethyl acrylate/maleic anhydride copolymers,
methyl acrylate/acrylic acid copolymers,
ethyl acrylate/acrylic acid copolymers,
methyl acrylate/maleic anhydride copolymers, and
ethyl acrylate/maleic anhydride copolymers.

6. The composition according to claim 1, wherein the stabilizer is a statistical copolymer of isobornyl (meth)acrylate and of $C_1$-$C_4$ alkyl (meth)acrylate wherein an isobornyl (meth)acrylate/$C_1$-$C_4$ alkyl (meth)acrylate weight ratio is greater than or equal to 5.

7. The composition according to claim 1, wherein the stabilizer is selected from the group consisting of:
isobornyl acrylate homopolymers,
statistical copolymers of isobornyl acrylate/meryl acrylate, statistical copolymers of isobornyl acrylate/methyl acrylate/ethyl acrylate, and
statistical copolymers of isobornyl methacrylate/methyl acrylate.

8. The composition according to claim 1, wherein the hydrocarbon-based oil is selected from the group consisting of apolar hydrocarbon-based oils.

9. The composition according to claim 1, wherein the content of hydrocarbon-based oil ranges from 20% to 75% by weight relative to the weight of the composition.

10. The composition according to claim 1, wherein the content of polymer particles surface-stabilized with a stabilizer, expressed as active material, represents from 5% to 55% by weight, expressed as polymer particle solids, relative to the weight of the composition.

11. The composition according to claim 1, further comprising a plasticizer selected from the group consisting of tri-n-butyl citrate, tripropylene glycol monomethyl ether and trimethyl pentaphenyl trisiloxane.

12. The composition according to claim 1, wherein the content of plasticizer represents from 1 to 50% by weight relative to the weight of the composition.

13. The composition according to claim 1, wherein the optionally modified clay is selected from the group consisting of modified hectorites, modified bentonites, and optionally modified silicas.

14. The composition according to claim 1, wherein the content of mineral thickener, expressed as active material, represents from 0.5% to 30% by weight relative to the weight of the composition.

15. The composition according to claim 13 wherein a content of the optionally modified clay, expressed as active material, ranges from 0.5% to 10% by weight relative to the weight of the composition.

16. The composition according to claim 13 comprising an optionally modified silica, wherein a content of the optionally modified silica, expressed as active material, is from 0.5% to 20% by weight relative to the weight of the composition.

17. The composition according to the preceding claim 16, wherein the composition is anhydrous.

18. A process for making up and/or caring for keratin materials, comprising applying the composition according to claim 1 to the keratin material.

19. The composition according to claim 8, herein the apolar hydrocarbon-based oils comprise from 8 to 16 carbon atoms.

20. The composition according to claim 13, wherein the optionally modified clay is selected from the group consisting of disteardimonium hectorite, stearalkonium hectorite, quaternium-18 bentonite, stearalkonium bentonite and quaternium-18/benzalkonium bentonite.

* * * * *